United States Patent [19]

Muderlak et al.

[11] Patent Number: 4,830,791
[45] Date of Patent: May 16, 1989

[54] ODOR CONTROL DEVICE

[75] Inventors: Kenneth J. Muderlak, Shorewood; Patrick D. Maloney, Madison, both of Wis.

[73] Assignee: Scentex, Inc., Chicago, Ill.

[21] Appl. No.: 162,021

[22] Filed: Feb. 29, 1988

[51] Int. Cl.$^4$ .............................................. B01F 3/04
[52] U.S. Cl. ....................................... 261/26; 239/35; 239/57; 250/215; 261/30; 261/96; 261/DIG. 17; 261/DIG. 65; 315/159; 422/124
[58] Field of Search ......................... 261/24, 26, 30, 96, 261/102, DIG. 17, DIG. 65; 239/35, 57, 60; 422/5, 123, 124; 250/211 R, 215; 315/159

[56] References Cited

U.S. PATENT DOCUMENTS

| | | | |
|---|---|---|---|
| 3,633,881 | 1/1972 | Yurdin | 261/DIG. 17 |
| 3,993,444 | 11/1976 | Brown | 261/DIG. 65 |
| 4,007,755 | 2/1977 | Lerner et al. | 261/DIG. 17 |
| 4,098,853 | 7/1978 | Brown et al. | 261/DIG. 65 |
| 4,166,087 | 8/1979 | Cline et al. | 261/DIG. 17 |
| 4,301,095 | 11/1981 | Mettler et al. | 261/DIG. 17 |
| 4,370,300 | 1/1983 | Mori et al. | 261/96 X |
| 4,383,951 | 5/1983 | Palson | 261/30 |
| 4,601,885 | 7/1986 | Hudgins | 261/DIG. 65 |
| 4,707,338 | 11/1987 | Spector | 422/124 |
| 4,743,406 | 5/1988 | Steiner et al. | 422/124 X |

FOREIGN PATENT DOCUMENTS 3209698 10/1983 Fed. Rep. of Germany ...... 422/124

Primary Examiner—Richard L. Chiesa
Attorney, Agent, or Firm—Laff, Whitesel, Conte & Saret

[57] ABSTRACT

An improved odor control device including a source of deodorizing olfactory stimuli, a squirrel cage fan for circulating air carrying the stimuli, an electronic circuit providing a visual indicia relating to the status of the power source. A secondary circuit controls indicia means for indicating the elapse of a predetermined span of time from initilization of control of one such span of time for the purpose of alerting the user to examine and/or replace the olfactory stimuli.

19 Claims, 2 Drawing Sheets

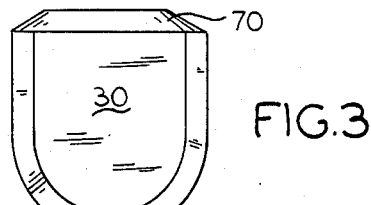
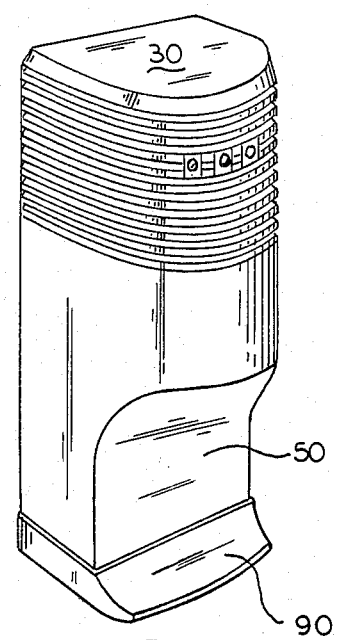
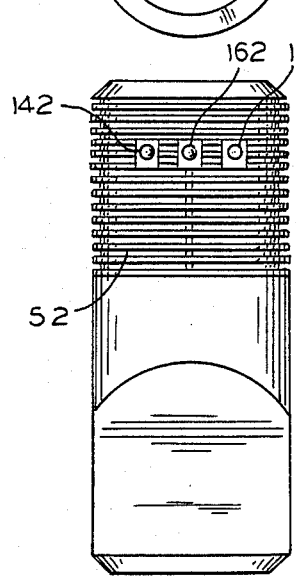
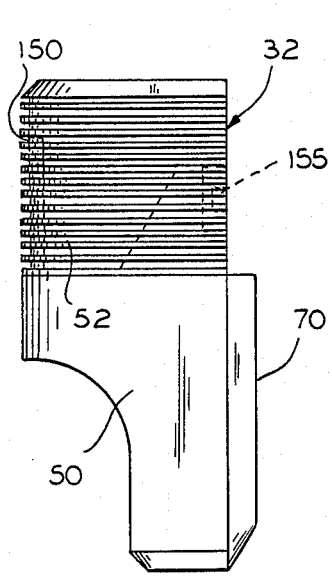
FIG.3
FIG.5
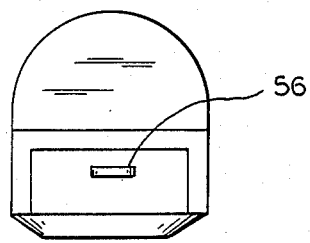
FIG.4
FIG.1
FIG.2
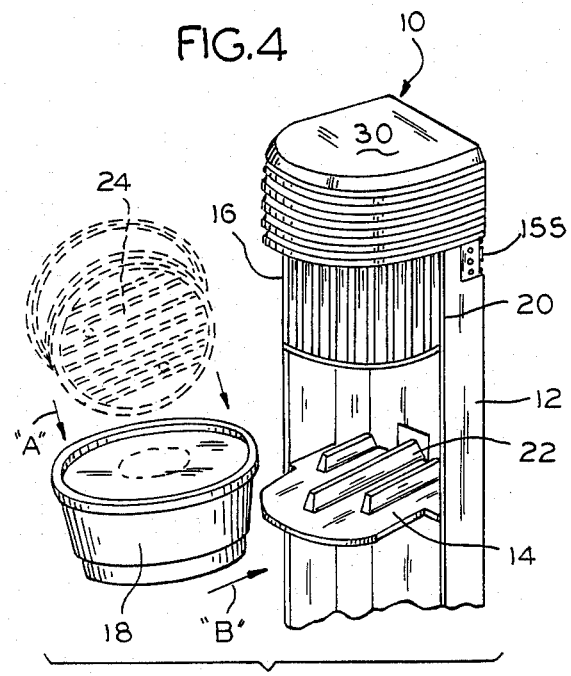
FIG.6
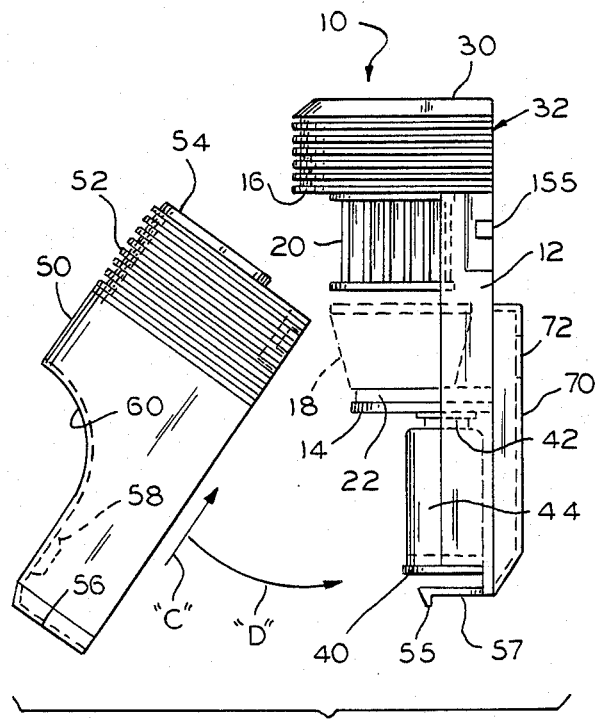
FIG.7

ODOR CONTROL DEVICE

This invention relates to an improved odor control device also known as an air freshener mechanism of the type generally utilized for providing olfactory stimuli which overcome the noxious odors commonly associated with public washrooms. There are many variations of air freshener units which include devices that supply a liquid odor producing substance into water as it is being flushed for coating the urinals and toilets during their flushing operation. Other devices involve both sprays and gels, the latter being inert and generally relying upon evaporation of the material from the gel or solid phase.

The present invention relates to a more positive type of device in which a powered fan exerts a circulating effect upon air that has been treated by a tub or container of an odoriferous material that serves as an olfactory stimuli. Major problems which confront the users of such devices in the prior art are either providing a specific electric outlet for their operation or providing dry cells for actuation of the fan units. Problems that exist in prior art devices are basically that there is nothing to tell the user when the fan has ceased operation through failure of the power source or alternatively when a predetermined time has elapsed since the actuation or installation of the device whereby the user can replace the gel or other material used for producing the olfactory stimuli. Other additional objections to the prior art are that they require a constant maintenance to determine the operational status as well as to determine the status of the supply of the olfactory stimuli.

SUMMARY OF THE INVENTION

The present invention contemplates an odor control device which will overcome most of the deficiencies of the prior art and includes a basic support structure for carrying the various elements in the design and which will in the long run provide a slim line design that includes a tamper proof casing which can be wall mounted or provided with suitable means for standing on a horizontal surface.

It is an object of the present invention to provide a squirrel cage fan member which can be revolved by a small battery operated motor tht is controlled by a light sensor wherein the sensor will turn the motor on and off during the presence or absence of a light source.

A further object of the present invention is to provide an indicator means for advising the user as to the go/on go status of the power source and the operation of the squirrel cage fan.

Still another object of the present invention is to provide a signal means capable of alerting the user of the elapse of a predetermined span of time from activation. The support means is further provided with orienting means for maintaining a container housing the olfactory stimuli in a fixed non-rotatable position subjected to the drawing power of the squirrel cage fan.

Still another object of the present invention is to provide a slim line, generally tamper proof, casing having a grill work that is aligned with the radial disposition of the squirrel cage fan whereby the olfactory stimuli can be dispersed through the grill into the ambient surrounding of the present device.

A still further object of the present invention is to provide a state of the art circuit technology which will conserve power, provide the desired indicia and will permit the use of a pair of 1.5 volt cells in parallel so that the device will operate over an extended period of time. These and other objects of the present invention will be apparent to those skilled in the art when the specification is read in conjunction with the attached drawing.

BRIEF DESCRIPTION OF THE DRAWING

FIG. 1 is a front vertical elevation of an odor control device of the type contemplated by the present invention;

FIG. 2 is a side elevational view of the device in FIG. 1;

FIG. 3 is a top view of the device in FIG. 1;

FIG. 4 is a bottom view of the device in FIG. 1;

FIG. 5 is another embodiment of the device shown in FIG. 1 wherein this secondary device is substantially identical to the first embodiment with the addition of a support means for maintaining the device in a vertical position relative to a horizontal surface;

FIG. 6 is an exploded view of the basic structure with a container of gel of the type contemplated for use in the present invention, the basic structure being shown with the cover removed;

FIG. 7 is an exploded side elevational view of the device shown in FIG. 2 with the cover removed to expose the internal positioning of various elements.

DESCRIPTION OF THE INVENTION

Figure 8:
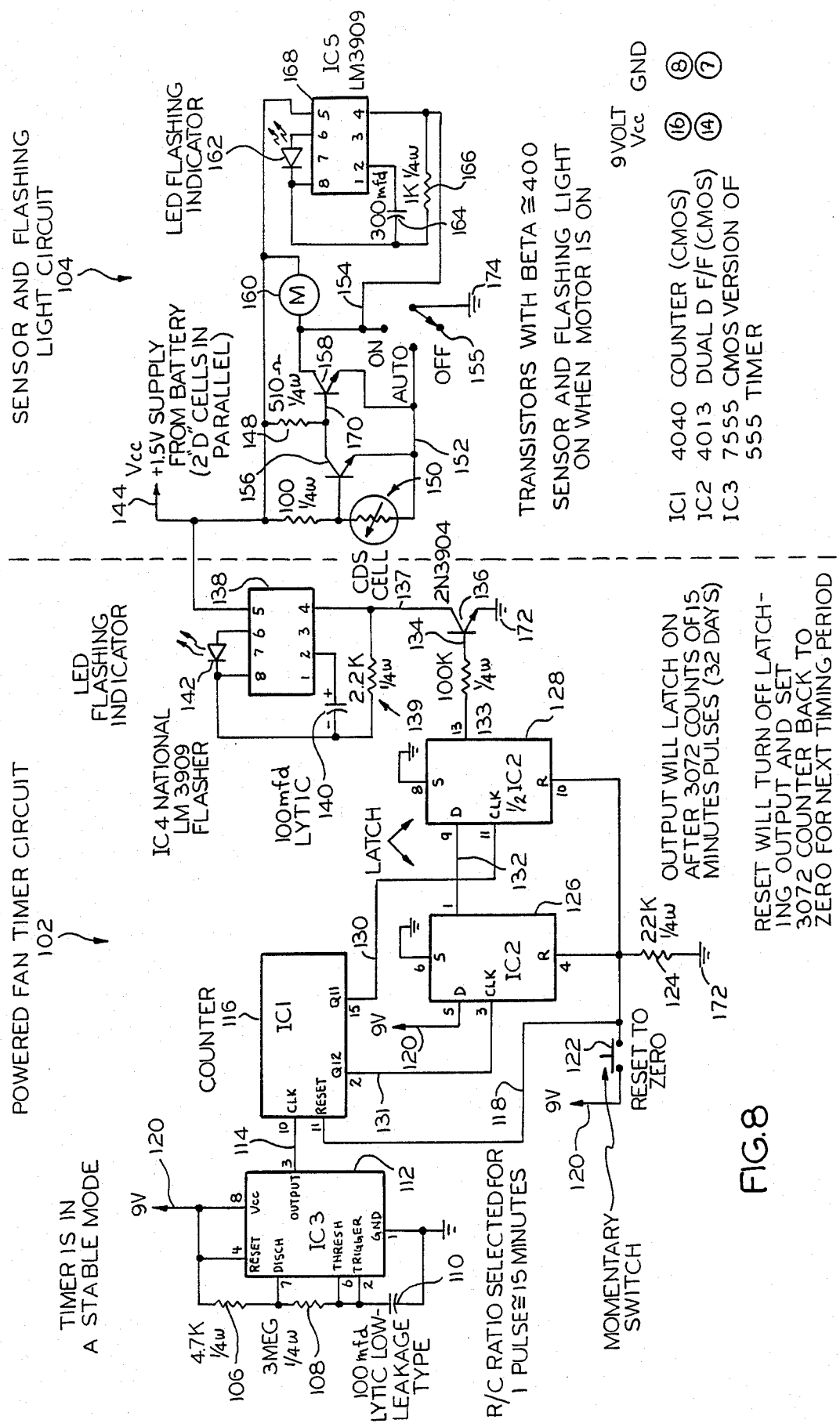
FIG. 8 is a schematic diagram of the circuitry utilized to control the motor for driving the squirrel cage fan in the present invention.

Referring now to the drawings wherein similar parts are designated by similar numerals, the improved odor control device 10, of the present invention, and as best seen in FIGS. 6 and 7, includes a generally channel shape elongated member 12 preferably made of a rigid insulating material, i.e. plastic material, which is divided into at least three zones. The first zone defined by a pair of laterally extending shelf means 14 and 16 define a space adapted to accept a container 18 of an olfactory stimuli such as an odoriferous gel 18 and an air movement inducing means 20 in the form of a squirrel cage rotor. The shelf 14 includes at least one rib-like projection 22 adapted to be complimentary accepted within at least one groove 24 on the underside of the container 18 (as shown in phantom in FIG. 6). The orientation of the grooves 24 being accomplished by rotation until positioned so that the container 18 can be swung downwardly as shown in the arrows designated "A" and then moved laterally into engagement with the at least one rib 22 in the direction designated by the arrow "B".

The second zone is a hollow chamber defined by the supporting shelf 16 and the top 30. The shelf 16 supports a motor (not shown) and the state of the art circuitry for control and operation of the device, not shown. The third zone, at the opposite end of the basic support unit 12 includes a shelf 40 and suitable electrical connectors 42 and 43 on the underside of shelf 14 and the upper surface of shelf 40, respectively, to support and engage at least one 1.5 volt dry cell 44. The circuitry of the connectors 42 is such that two dry cells can be supported in a parallel circuit to provide a more extended life and usage in the present device.

To provide a closed esthetic appearance a cover 50 is utilized which is generally simi-circular in configuration and has an open grill work 52 at its upper end for disposition adjacent the squirrel cage 20 and capable of accepting the ingress and egress of moving air through the grill work. The upper end includes a shoulder means 54 that is compatible with and cooperatively accepted within a complimentary groove, not shown, in the undersigned of shelf 16, as viewed in FIG. 7. When the shoulder or rib 54 is introduced into the groove by movement in the direction of the arrow "C" the cover 50 is swung in the direction of the arrow "D" until a slot 56 in its bottom is captured by a tang 55 carried on a spring arm 57, the arm 57 being fastened to the rear wall of the basic structure 12. This then provides a configuration substantially identical to that shown in FIGS. 1–5.

The basic support structure also includes a switch means 155 located near its upper end and in association with the power source as well as the circuitry contained in the upper housing. The switch 155 has three positions of off, auto, and on; the action of switch 155 being described in detail hereinafter.

Extending outwardly from the back plane of the basic structure 12 is a lateral box-like extension 70 which includes one or more aperture means 72 for acceptance of suitable fastener means for maintaining the basic structure in parallel juxtaposed relation to a supporting wall.

It will be noted in FIGS. 1, 2 and 5 that the upper housing 32 of the basic structure includes at least one, and in the presnt embodiment three openings for accommodating and exposing various elements to ambient. Two of the items shown in FIG. 1 namely 142 and 162 are light emitting devices, such as light emitting diodes. The third opening accommodates a light sensing means 150 which, in the form of the present invention, is a cadmium sulfide cell.

Referring now more specifically to FIG. 8, the upper housing 32 includes a pair of circuits 102 and 104. Circuit 102 is a powered fan timer circuit while circuit 104 is a sensor and flashing light circuit.

As was previously indicated, one of the object of the present invention is to provide indicia means for notifying the user of such an odor control device as to the go/on go condition and operation of the blower motor. The sensor and flashing light circuit 104 controls the operation of a blower motor 160, seen in FIG. 8, and an LED indicator 162. When the control switch 155 is set to the "on" position, the blower motor 160 and flashing LED indicator 162 operates continuously. When the control switch 155 is set to the "auto" position, the blower motor 160 and flashing LED indicator operate only when the light sensor 150 detects light.

A cadmium sulfide (CdS) photocell 150 is used as a light sensing device. The photocell 150 and resistor 146 form a voltage divider which controls the bias applied to the base of transistor 156. When exposed to relative darkness, the resistance of photocell 150 is high and transistor 156 is turned on, inhibiting transistor 158. When exposed to normal room light, the resistance of photocell 150 decreases. This inhibits current to resistor 146 into the base of transistor 156 and causes it to turn off. The voltage at signal 170 increases enabling current to flow into the base of transistor 158, causing it to conduct. When switch 155 is set to the "auto" position, transistor 158 completes the negative power supply path for the blower motor 160 and flasher circuit 168 to a common ground 174. Thus, these devices operate only when photocell 150 is exposed to room light.

If desired, switch 155 can be set to the "on" position and then the negative power supply path to the lower motor 160 and flasher circuit 168 is connected directly to ground and these devices will operate continuously. It sould be recognized, however, that when the motor runs continuously that the drain on the power supply is substantially greater than the intermittent or auto operation and hence the life span of the power source would be shorter. IC 168, a commercially available type LM3909 flasher circuit, alternatively supplies power to and removes power from LED 162, causing it to flash. The capacitor 164 and resistor 166 determine the rate at which LED 162 flashes. The flasher 168 and blower motor 160 obtain their positive power supply 144 from at least one 1.5 volt cells. But preferably two 1.5 volt cells are connected in parallel and thereby provide a longer life for the operation of the unit.

Thus, the sensor and flashing light circuit 104 advises the user of an odor control device of this type of the operation of the squirrel cage motor and its throw-out of the olfactory stimuli into the surrounding ambient. The flashing light LED 162 is chosen since a constant light source from LED's is not easily recognizable and there is a tendency for LED's to not only dim after extended continuous usage but also to give the optical illusion of blending color wise into their surrounding environment. It has been found that the flashing light provides a better visual stimuli for determining the status or state of a circuit.

The user of the "auto" position again saves energy and only will activate the spinning of the squirrel fan and the throwing off of the olfactory stimuli during the presence of someone in the facilities or room where the device is positioned and when the lights are on in that room. The absence of lights causes the entire device to stop and to stop drainage on the power source.

A second circuit which can be incorporated into the preferred embodiment is a powered fan timer circuit. Such a circuit will keep the device operating for a predetermined span of time, for example it has been found that the usage or life of a container of olfactory stimuli material is generally in the range of thirty days. To ensure that an adequate supply of gel is installed in the device this timer circuit serves a desireable function in that it will permit operation of the device without interruption but at the end of the predetermined span of time it will trigger a second LED flashing indicator 142 to advise the user of such a device that the olfactory stimuli or gel in the container 18 should be checked and/or replaced.

Referring now to FIG. 8, the powered fan timing circuit 102 illustrated provides a visual indication that approximately thirty-two days have passed since either the operation of the device was initiated or since reset switch 122 was last pressed.

In brief, integrated circuit (IC) 112 is a timer and preferably an astable timer which repetitively provides a short pulse after each interval of a predetermined time. In the present instance this time span is 15 minutes between pulses. IC 116 is a multi-stage binary counter which counts each pulse from timer 112 and supplies a binary value representing the number of received pulses on its output terminals. Latch signal devices 126 and 128 are C-type flip-flops which are adapted to recognize when counter 116 has received 3,072 pulses. At 15 minutes between individual pulses, 3,072 pulses represents a period of 32 days. When this event occurs, flip-flop 128 turns on flasher IC 138. IC 138 is a commercially available circuit which alternately supplies power to and removes power from the light emitting dial indicator 142, causing it to flash.

In more detail, IC 112 can be a commercially available type 7555 CMOS timer circuit, used here in its astable (repetitive) mode. Resistors 106 and 108, with capacitor 110 (a low leakage electrolytic capacitor), form a network which determine the time period for timer 112, in the present instance approximately 15 minutes between pulses. Each time the set predetermined period elapses, timer 112 supplies a short pulse on signal 114, the clock input of IC 116. IC 116 is a commercially available type 4040 countercircuit. Counter 116 present a binary value equal to the number of pulses received from timer 112 on its output terminal. In this circuit, only output bits 11 (signal 130) and 12 (signal 131) are needed; the other available outputs being unused. Devices 126 and 128 are each half of a commercially available type 4013 dual D-type flip-flop IC, used to recognize that counter 116 has reached 3,072 counts.

Switch 122 a momentary contact switch is actuated by the user to reset the 32 day timing interval. When actuated, this switch asserts signal 118, resetting counter 116 and flip-flops 126 and 128. Resistor 124 is a pull-down resistor which negates signal 118 when the switch is not actuated. Starting from an initialized state, counter 116 counts pulses from timer 112. When counter 116 has received 2,048 pulses, it asserts output bit 12 (signal 131), causing flip-flop 126 to propagate data from its wired-high D input to the output. This asserts signal 132 to the D input of flip-flop 128. This activates flip-flop 128 so that when counter 116 has received 3,072 pulses it asserts output bit 11 (signal 130) causing flip-flop 128 to clock the "high" on its D input to the output, asserting signal 133.

IC 138, a commercially available type LM3909 flasher circuit, obtains its negative power supply from ground 172 through transistor 136. Asserted signal 133 from flip-flop 128 provides drive current through resistor 134 to the base of transistor 136, causing it to conduct, enabling flasher 138. Flasher circuit 138 alternatively supplies power to and removes power from LED 142 causing it to flash. Capacitor 140 and resistor 139 determine the rate at which LED 142 flashes. Flasher 138 obtains its positive power supply 144 from the aforementioned two 1.5 volt cells (connected in parallel). It should be noted that the ground 172 and the ground 174 are common throughout the two circuits and that the timer and the counters utilize a nine volt source 120 which is common throughout the second mentioned circuit 102.

An alternate embodiment to flasher 138 might employ a flasher circuit composed of discrete components instead of the LM3909 flasher as shown in FIG. 8 as IC 168 or IC 138. Such an approach might reduce cost in manufacturing situations where labor is inexpensive.

Referring now to FIG. 5, in a second embodiment it will be seen that the lower cover 52 and the lower extremity of the basic structure 12 are accepted into a base-like support 90 that has a hollow cavity for accepting the relatively rectangular end of the cover 50 and the basic structure 12 to support the entire oder control device on a horizontal surface in an upright position.

While other embodiments will become apparent to those skilled in the art, it is the intent that this application be limited solely by the appended claims.

We claim:

1. An improved odor control device including a basic support structure, power means, means for creating air-movement driven by said power means, a source of deodorizing olfactory stimulating means, means for determining the operation of said means for creating air-movement whereby the status of operability of said power means can be ascertained, means for determining a predetermined life span based on the operation of said device, the normal life of said deodorizing olfactory stimulating means being substantially equal to said predetermined life span, wherein said means for determining said predetermined life span includes a timer, a separate power source for driving said timer, said timer generating periodic pulses at predetermined intervals, a counter means accepting said periodic pulses, said counter means generating a latch signal upon receipt of a predetermined number of periodic pulses, signal means activated by said latch signal for notifying the user of said odor control device of the need for replacement of said deodorizing olfactory stimulating means.

2. An improved odor control device of the type claimed in claim 1 wherein said device includes means for permitting operation of said device only when subjected to a light source, thereby conserving said power source.

3. An improved odor control device of the type claimed in claim 2 wherein said mens for determining the operation of said means for creating air-movement includes a circuit means having a flasher control means and a light emitting diode connected in parallel with said motor means to said power source.

4. An improved odor control device of the type claimed in claim 8 wherein said means for permitting operation of said device only when subjected to a light source includes a light sensing device having the capability of providing an off or an on signal, respectively, in the absence or presence of a light source, means for amplifying the signal from said light sensing device connected to said power source and to said motor, thereby conserving the power source for use only when said light sensing device is subjected to light as when someone turns on a light in an enclosed room wherein said odor control device is located.

5. An improved odor control device of the type claimed in claim 4 wherein said amplification means includes at least one transistor means biased by an appropriate resistance, said transistor being in series with said motor and said transistor with its resistance being in parallel with said light sensing device and said power source.

6. Am improved odor control device of the type claimed in claim 5 wherein said light sensing device is a cadmium sulfide light sensor.

7. An improved odor control device of the type claimed in claim 5 wherein said circuit also includes manual switch means that has three positions, one position being off, the second position directly connecting said motor to ground and hence causing continuous operation of said motor, and the third position connecting said transistor means to ground and subjecting motor to the control of the light sensing device.

8. An improved odor control device of the type claimed in claim 1 wherein said means for creating air-movement is an electric motor driving a squirrel cage fan, said basic support structure adapted to carry a removeable type cover having an open grill that permits passage of said air-movement through said open grill and prevents inadvertent engagement with said cage fan during its operation.

9. An improved odor control device of the type claimed in claim 8 wherein said means for determining the operation of said cage fan includes circuit means for powering a flashing light means visible externally of said basic support structure to a casual observer.

10. An improved odor control device of the type claimed in claim 9 wherein said circuit means includes a flasher control means and a flasher light means in the form of a light emitting diode connected in parallel with said motor means to said power source.

11. An improved odor control device of the type claimed in claim 8 wherein said basic support structure is normally disposed in a vertical array and includes at least three distinct zones, a first zone having shelf means for supporting said deodorizer and spaced from said shelf means is said cage fan means, said deodorizer being exposed to the air flow created by said cage fan means to thereby disburse same into the ambient surrounding said device, a second zone divided by suitable support means from said first zone, motor means for driving said fan, said suitable support means carrying said motor and its connected fan, and a third zone containing said power source, said open grill in said removeable cover being so oriented as to be immediately adjacent said cage fan and permit olfactory stimuli to be disbursed into the ambient atmosphere surrounding said basic support structure.

12. An improved odor control device of the type claimed in claim 8 wherein said odor control device includes an accessory element complimentary to said cover and capable of accepting same to provide a free standing support element for said odor control device to permit said device to be maintained in an upright position on a horizontal surface, as for example, a table or desk.

13. An improved odor control device of the type claimed in claim 1 wherein momentary switch means are provided to apply a momentary predetermined voltage to said counter device to reset same to zero for purpose of establishing the next timing period.

14. An improved odor control device of the type claimed in claim 1 wherein said means for determining the operation of said means for creating air-movement includes a first flashing light means, said signal means includes a second flashing light means, said first and second flashing light means being of different colors to advise the user of said device the status of its operation.

15. An improved odor control device of the type claimed in claim 14 wherein said signal means includes a flasher means, capacitor means, resistor means and a light emitting diode means, said flasher means activated by a transistor latched by said counter circuit to connect one terminal of said flasher means to ground while another terminal thereof is connected to a voltage power supply.

16. An improved odor control device of the type claimed in claim 1 wherein said basic support structure includes means for accepting fastening means to maintain said support structure in juxtaposed relation to a wall support.

17. An improved odor control device of the type claimed in claim 16 wherein said means for accepting fastening means includes a recessed extension to said basic support structure entending laterally rearwardly therefrom and including aperture means for positive location and retention of said fastening means.

18. An improved odor control device of the type claimed in claim 1 wherein said power means includes a 1.5 volt power supply from at least one 1.5 volt dry cell.

19. An improved odor control device of the type claimed in claim 18 wherein said power means includes a 1.5 volt power supply from two 1.5 volt dry cells in parallel to insure continuous operation at full power for a longer period of time.

* * * * *